United States Patent [19]

Meilland

[11] Patent Number: Plant 7,383

[45] Date of Patent: Nov. 20, 1990

[54] ROSE PLANT — MEIGROUGE VARIETY

[75] Inventor: Alain A. Meilland, Antibes, France

[73] Assignee: The Conard-Pyle Company, West Grove, Pa.

[21] Appl. No.: 354,283

[22] Filed: May 19, 1989

[51] Int. Cl.[5] ..... A01H 5/00

[52] U.S. Cl. ..... Plt./20

[58] Field of Search ..... Plt./20, 21

[56] References Cited

U.S. PATENT DOCUMENTS

P.P. 3,452 1/1974 Meilland ..... Plt/21

P.P. 4,037 4/1977 Paolino ..... Plt. 20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which forms in abundance attractive fully double long lasting blossoms which are strawberry red on the upper surface and cardinal red on the under surface. The plant exhibits vigorous vegetation and an erect growth habit. The new variety exhibits an excellent capability for greenhouse forcing during cut flower production. Excellent resistance to fungal diseases also is manifest.

1 Drawing Sheet

SUMMARY OF THE INVENTION

The new variety of Hybrid Tea rose was created by artificial pollination wherein two parents were crossed which previously had been studied in the hope that they would contribute the desired characteristics. The female parent (i.e., the seed parent) of the new variety was the Meired variety U.S. Plant Pat. No. 3,452). The Meired variety sometimes is known as the VISA variety in the United States. The male parent (i.e. the pollen parent) of the new variety was the Royalty variety (U.S. Plant Pat. No. 4,057). The parentage of the new variety can be summarized as follows:

Meired × Royalty.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive fully double long-lasting blossoms which are strawberry red on the upper surface and cardinal red on the lower surface,
(b) exhibits an erect growth habit,
(c) forms vigorous vegetation,
(d) exhibits an excellent greenhouse forcing capability, and
(e) exhibits exellent resistance to cryptogamic diseases.

The new variety is totally different than its Meired parent in plant habit, foliage, bud shape and opening. Also, the new variety is superior in overall bloom production than Meired since its cycles more quickly when forced in a greenhouse and exhibits better winter production.

The foliage of the new variety is similar to that of its Royalty parent; however, the bud shape and opening are different. Also, the new variety exhibits a more compact growth habit than Royalty and is accordingly more easy to manage by flower growers. The blossoms of the new variety are more like those of Forever Yours U.S. Plant Pat. No. 2,443). than those of either of its parents. Forever Yours is a parent of Royalty.

The new variety well meets the needs of the horticultural for all uses and is well-suited for the production of cut flowers. The greenhouse forcing capacity of the new variety during the winter is particularly noteworthy.

The new variety has been found to undergo asexual propagation by a number of routes, including budding, grafting, cuttage, etc. The characteristics of the new variety have been found to be strictly transmissable by such asexual propagation from one generation to another.

The new variety has been named the Meigrouge variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and observed during November while budded on *Rosa indica* understock and growing in greenhouses at Cap d' Antibes, France.

DETAILED DESCRIPTION

Figures 1, 2, 3, 4, 5, 6, 7, 8, 9, 10, 11, 12, 13, 14, 15, 16:
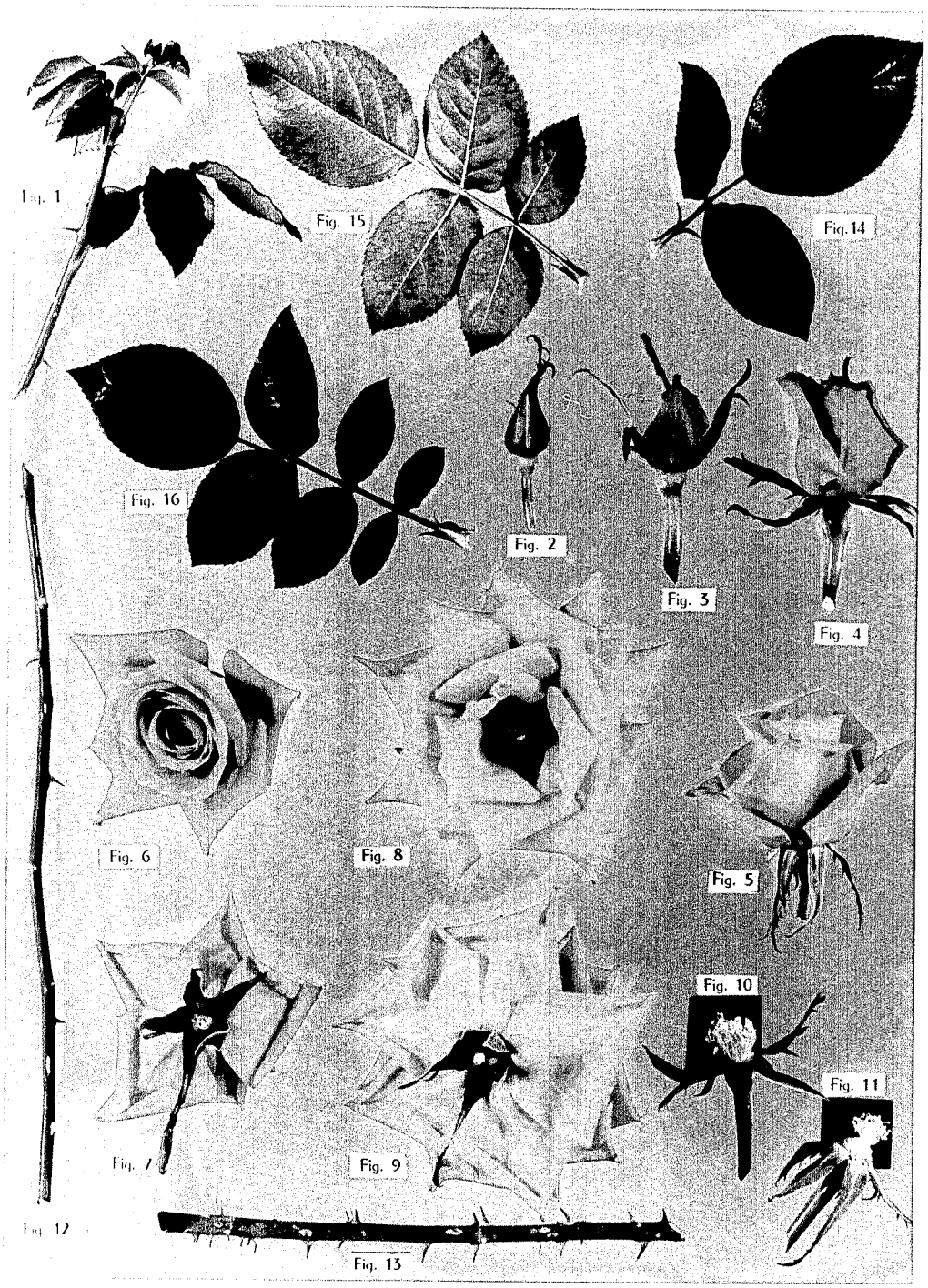
FIG. 1 illustrates a specimen of a young shoot.
FIG. 2 illustrates a specimen of a floral bud before the opening of the sepals.
FIG. 3 illustrates a specimen of a floral bud when the sepals open.
FIG. 4 illustrates a specimen of a floral bud when the petals open.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a section of a flowering stem.
FIG. 13 illustrates a specimen of a section of a main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.

The chart used in the identification of the colors is that of The Royal Horticultural Society (R.H.S. Colour Chart). The description is based on observations of two year old specimens made during November while budded on *Rosa indica* understock and growing in greenhouses at Cap d' Antibes, France. Color terminology in common terms precedes the reference to such chart.

Class: Hybrid Tea.

Plant:

Height.—Plants which were pruned to a height of 85 cm. commonly produce floral stems having a length of approximately 40 to 60 cm.

*Habit.*—Erect.

Branches:

*Color.*—Young stems: medium green, Yellow-Green Group 146B, more or less stained with reddish brown. Adult wood: bronze green, Yellow-Green Group 146A.

*Thorns.*—Size: medium. Quantity: average to numerous. Color: pinkish-green on young stems and greenish changing to tan on mature wood.

Leaves:

*Stipules.*—Adnate, pectinate, wide and linear.

*Petioles.*—Upper surface: striped, reddish green on young foliage and medium green on adult foliage with more or less glandular edges. Under surface: light green, bear a few glandular prickles.

*Leaflets.*—Number: 3, 5 (most often), 7, and 9. Sometimes the leaflets are incomplete and malformed. Serration: single and regular. Texture: consistent. General appearance: foliage is dense and semi-dull. Color (young foliage): Upper Surface: lettuce green, Yellow-Green Group 144A, more or less stained with reddish coloration. Under surface: light green suffused with reddish coloration. Color (adult foliage): Upper surface: dark green, Green Group 137A. Under surface: light green, Green Group 137C.

Inflorescence:

*Number of Flowers.*—Generally one per stem.

*Peduncle.*—Straight, upright, rigid, light green in coloration, more or less glandular, approximately 10 to 12 cm. in length on average.

*Sepals.*—Upper surface: tomentose, greenish in coloration. Under surface: medium green in coloration, smooth, the outside sepals have edges which are more or less appendiculated.

*Buds.*—Shape: conical and somewhat elongated. Length: approximately 3.5 to 4 cm. on average. Size: large. Color upon opening: Upper Surface: cardinal red, Red Group 53B. Under surface: dark cardinal, Red Group 53A.

*Flower.*—Shape: cuplike and fully double. Diameter: approximately 9 to 11 cm. on average. Color (when opening begins): Upper surface: dark bright strawberry, Red Group 46C. Under surface: cardinal red, Red Group 53B. Color (when blooming): Upper surface: dark bright strawberry, Red Group 46C. Under surface: light cardinal red, Red Group 53C. Color (at end of opening): Upper surface: cardinal red, Red Group 53B. Under surface: light cardinal red, Red Group 53C. Fragrance: none. Lasting quality: long either on the plant or in a vase. Petal number: approximately 40 to 45 on average. Texture: consistent. Petal drop: good. Stamen number: approximately 127 to 135 on average. Anthers: strawlike with a pinkish center. Filaments: light fuschia, of generally regular height. Pistils: approximately 106 to 116 on average. Stigmas: normal and strawlike. Styles: strawlike with fuschia tip, more or less twisted, tomentose at base, of irregular heights. Receptacle: light green and in longitudinal section is pear-shaped.

Development:

*Vegetation.*—Vigorous.

*Blooming.*—Very floriferous.

*Aptitude to forcing.*—excellent.

*Resistance to diseases.*—Excellent.

I claim:

1. A new and distinct variety of Hybrid Tea rose plant characterized by the following combination of characterstics:

(a) forms in abundance attractive fully double long-lasting blossoms which are strawberry red on the upper surface and cardinal red on the lower surface,
(b) exhibits an erect growth habit,
(c) forms vigorous vegetation,
(d) exhibits an excellent greenhouse forcing capability,
(e) exhibits excellent resistance to cryptogamic diseases;

substantially as herein shown and described.

* * * * *